United States Patent [19]

Moreau et al.

[11] Patent Number: 5,075,231
[45] Date of Patent: Dec. 24, 1991

[54] LIPASES AND LIPASE EXTRACTS, THEIR PREPARATION PROCESS AND THEIR THERAPEUTIC USE

[75] Inventors: Hervé Moreau; Robert Verger, both of Marseilles; Daniel Lecat, Paris; Jean-Louis Junien, Sevres, all of France

[73] Assignee: Jouveinal S.A., Paris, France

[21] Appl. No.: 97,896

[22] Filed: Sep. 17, 1987

[30] Foreign Application Priority Data

Sep. 17, 1986 [FR] France ............................... 86 12996

[51] Int. Cl.$^5$ ........................ C12N 9/20; A61K 37/54
[52] U.S. Cl. ................................... 435/198; 424/94.6; 435/134
[58] Field of Search ................ 435/198, 134; 424/94.6

[56] References Cited

FOREIGN PATENT DOCUMENTS 8601532 3/1986 World Int. Prop. O. .

OTHER PUBLICATIONS

Negre, A. et al., (1984), Biochim. Biophys. Acta 794, 89-95.
Bernback, S. et al., (1987), 922, 206-213.
Hamosh, M. et al., (1979), J. Biol. Chem. 254(23), 12121-12125.
Hamosh, M. et al., (1981), J. Clin. Invest. 67, 838-846.
Tiruppathi, C. et al., (1982), Biochim. Biophys. Acta 712, 692-697.
Fink, C. S. et al., (1985), Am. J. Physiol. 248, 68-72.

*Primary Examiner*—Elizabeth C. Weimar
*Assistant Examiner*—Charles L. Patterson, Jr.
*Attorney, Agent, or Firm*—Cushman, Darby & Cushman

[57] ABSTRACT

Process for the preparation of a gastric lipase. The stomachs of rabbits or horses undergo extraction by an acid aqueous medium, the lipase extract is salted out by the addition of hydrosoluble salts then, by filtration on a molecular sieve, followed by separation using ion exchange chromatography, an elution fraction containing the lipase is collected.

Medicament for fighting against malabsorptions of fatty substances.

22 Claims, No Drawings

LIPASES AND LIPASE EXTRACTS, THEIR PREPARATION PROCESS AND THEIR THERAPEUTIC USE

The present invention relates to enzymes having a lipase activity and to the extracts containing them, which are stable, active products in media which are acid or close to neutrality, their preparation process and their use in therapy in the form of medicaments.

Lipases, which are enzymes related to hydrolases, occur in organisms as different as bacteria, fungi, plants and animals. Their importance in the functions of living matter was recognized in about 1900 during the study of the digestion phenomenon. Their function has proved to be essential for the assimilation of fatty matter representing an important energy source in human and animal food. Subsequently their properties have been utilized for therapeutic purposes.

Numerous studies have been carried out in man and mammals in general. They have revealed the essential catalytic function of these enzymes during digestive phenomena, where they are more particularly involved in hydrolyzing emulsified or non-emulsified fats. The latter are largely formed from esters formed between fatty acids of various molecular weights and monofunctional or polyfunctional alcohols, such as glycerol in the case of triglycerides. The lack or deficiency of these enzymatic systems has frequently been noted in the case of malabsorption, whose sometimes serious consequences can lead to considerable weight losses and to marked anorexic states. In man, these states, which can attack both young children and adults, have justified the therapeutic use of exogenous enzymatic systems in order to compensate the natural lipase deficiencies in these patients. The compositions used have involved animal organs for their extracts, whose lipase secretion has been recognized and which normally act in the organism for the assimilation of fats. These organs are located at different levels of the bucco-gastro-intestinal tract, the most widely known being those of the oral cavity and pancreas.

The secretions of the oral cavity of mammals consequently contain enzymes able to hydrolyze fatty acid esters. These are pregastric esterases and "oral" lipases, which only differ from one another by their capacity of being active on hydrolyzable or non-hydrolyzable substrates. These enzymes and their properties have formed the subject matter of numerous works summarized by J. H. Nelson et al (Journal of Dairy Science, 1976, 60 (3), pp. 327-362).

Their presence and their usefulness have in particular been demonstrated in unweaned young animals. Consequently, the marketing of pregastric esterases obtained from calves, kids and lambs has made great strides. These products, firstly in the form of liquid extracts and then concentrated powders, are currently used in veterinary medicine in the treatment of diarrhoea of calves and also in human therapy, as described in U.S. Pat. No. 3,256,150, which describes a method for the treatment of the malabsorption syndrome by means of a composition in powder form, which is orally administered. This composition partly comprises edible tissues taken from the oral cavity of unweaned animals and more particularly the tongue and adjacent tissues taken from the calf, kid or lamb. The latter use does not appear to have had much success probably due to the difficulties in collecting large quantities of organs taken after the sacrificing of young animals intended for food and which have not yet developed to an economically viable extent.

To obtain freedom from these practical and economic problems, British patent 2 142 337 proposes a lingual lipase of the rat or man for treating lipase deficiencies. These enzymes are prepared by genetic engineering.

At the duodenal level, lipases of the pancreatic juice have also a very significant activity for the assimilation of partly degraded or non-degraded fatty matter. Thus, a deficiency in enzymatic secretion of the pancreas can lead to malabsorption phenomena which, for fatty matter sometimes lead to abnormalities in the digestion and assimilation of such matter. In man, pancreatic substitution medicaments administered by the oral route have been marketed in the form of composition based on the pancreas of animals, whose food is similar to that of man, such as the pig, or having herbivora-type food, such as cattle. However, the study of the properties of these enzymes, particularly by Gunter Cordes in 1973 Deutsche Apothekerzeitung No. 47, November 1973 pages 1855-1857, Bestimmung der Zerfallszeit von Tabletten has demonstrated the precariousness of such treatments. The enzymatic systems of these organs are rapidly destroyed and deactivated in an acid medium at 37° C. and in themselves are unable to ensure the activity thereof following a gastric transit. Solutions have been proposed for preserving the activity of these medicaments. British patent 1 139 991 describes a composition comprising pancreatic enzymes associated with salts with antacid properties, whose function is to preserve the properties of the enzymes during transit by reducing natural gastric acidity. An identical procedure has been proposed by Regan P. T. et al (1978) (Mayo Clin. Proc. 53, 79-83.1978. Rationale for the use of Cimetidine in Pancreatic insufficiency), Van S. Hubbard (The American Journal of Clinical Nutrition 33: November 1980 pp. 2281-2286; Effectiveness of cimetidine as an adjunct to supplemental pancreatic enzymes in patients with cystic fibrosis and Gow (The Lancet, Nov. 14, 1981 pp. 1071-1074 Comparative study of varying regimens to improve creatorrhoea in cystic fibrosis, using H2 receptor antagonist compounds, such as cimetidine.

Moreover, attempts have been made to preserve the activity of enzymes by coating medicaments with a gastro-resistant film, which is soluble in the intestinal medium and releases the active principles in the duodenum, or more recently by including them in microspheres with a diameter of close to 3 mm. These solutions are only palliative and have risks of side effects in the patient or an uncertain efficacy.

Thus, pancreatic affections often require long-lasting treatment, during which the repeated reduction of the gastric acidity can give rise to a local reduction of natural defences to bacteria and the proliferation of the latter, as has been described by Weber A. M., 1982 (Proc. 11th annual meeting European working—Cystic fibrosis Brussels—Belgium—1982 lecture ref. 91 pp. 187-195 Fat malabsorption in Cystic fibrosis: mechanisms and treatment) and whose consequences are dramatic in the case of alimentary intoxication.

Coating of the products cannot ensure a total safety of use in certain cases, such as pancreatic insufficiency, where irregular pH values have been found in the gastro-intestinal tract, sometimes with abnormal acid levels, which are incompatible with the dissolving of the gastro-protective membrane at the desired point.

The presence of lipase activity in the gastric content of different animal species has also been noted. The origin of this activity has long been subject to controversy and has been attributed either to oral secretion transported by the saliva, or to a duodenal reflux of the pancreatic juice. However, recently Fink C. S. et al (Am. J. Physiol., 1985, 248, pp. 68–72) have demonstrated on the basis of a dispersion of gastric rabbit glands, a lipase activity whose effect is at a maximum from pH 5.8 to 6.1. In Chemical Abstracts, vol. 97, no. 15, 11.10.1982, p. 477, no. 1248320, Columbus, Ohio, U.S.A., reference is made to a lipolytic activity at the gastric level in the weaned or unweaned young rabbit. This activity reaches a maximum at a pH of 7. Patent application WO 86/01532 describes the preparation by genetic engineering of a protein corresponding to a human gastric lipase useful for the treatment of cases of deficiency of said enzyme.

The research carried out on lipases and the attempts to use them clearly show the importance attributed to these enzymes and, although their presence has been demonstrated in certain organs and secretions of mammals and their need for the assimilation of fatty matter by the organism has been recognized, hitherto no lipase or lipase composition has been proposed having a technically and economically viable preparation and which, by compensation, is able to reliably ensure said assimilation of fatty matter and in particular triglycerides throughout the bucco-gastro-intestinal tract.

The present invention breaks with this state of the art by relating to lipases and lipase extracts, whose activity is not deteriorated by spending time in the acid medium and which effectively develop their aptitude to hydrolyzed triglycerides in media whose pH ranges from 3 to 7, i.e. in media having an acidity compatible with that for the use thereof throughout the bucco-gastro-intestinal tract. Thus, compared with the products described in the prior art, the inventive products have an undeniable advantage, particularly in therapy, as a result of their aptitude to reliably ensure during digestion the hydrolysis of triglycerides along the tract between the oral cavity and the duodenum, whilst coming from raw materials which are readily accessible in large quantities and at low price.

The present invention therefore relates to a process for the preparation of lipase extracts or a lipase, characterized in that it comprises:

a) for obtaining a lipase extract:

bringing the adult horse or rabbit stomach fundus into contact with an acid aqueous medium having a pH of 1.5 to 5, at a rate of 1 to 10 parts by volume of the acid medium for 1 part by weight of fundus, at a temperature of 4° to 30° C. and for between 1 minute and 15 hours to obtain solid materials and an aqueous solution containing a lipase part, separating the aqueous solution from the solid materials to obtain a separate aqueous solution, adding to the separate aqueous solution an adequate quantity of hydrosoluble salt and leaving it there for a time adequate for salting out the sought lipase extract and for obtaining a supernatant solution and separating the sought lipase extract from the supernatant solution and collecting it;

b) for obtaining a desalted lipase extract:

dissolving the lipase extract in an aqueous phase, filtering the aqueous phase on a membrane having a cutoff threshold between 5,000 and 10,000 daltons for obtaining a solution of the desalted lipase extract and lyophilizing the desalted lipase extract solution into desalted lipase extract;

c) for obtaining a delipidated lipase extract:

also carrying out a delipidation operation on any random one of the solid parts containing the lipase extract constituted by the stomach fundus, the lipase extract and the desalted lipase extract;

d) for obtaining a non-delipidated, enriched lipase extract:

dissolving the lipase extract in a pH buffer between 2 and 7 to obtain a buffered solution, subjecting the buffered solution with a pH between 2 and 7 to chromatography on a molecular sieve, whose exclusion limit exceeds 1,000,000 daltons and collecting the excluded elution fraction containing the non-delipidated, enriched lipase extract in buffered solution, filtering said excluded elution fraction on a membrane having a cutoff threshold of 10,000 daltons for obtaining a desalted fraction and lyophilizing this desalted fraction into the sought, non-delipidated, enriched lipase extract;

e) for obtaining a delipidated, enriched lipase extract:

e)1 dissolving the lipase extract in water for obtaining an aqueous solution containing the lipase extract, filtering the aqueous solution containing the lipase extract on a membrane having a cutoff threshold between 5,000 and 10,000 daltons for obtaining a salt-free solution, adsorbing the salt-free solution on an ion exchange support, desorbing the support by an eluent, whose ionic strength is progressively increased as a function of time, collecting an elution fraction having a lipase activity and containing the delipidated, enriched lipase extract, filtering the elution fraction having a lipase activity on a membrane having a cutoff threshold between 5,000 and 10,000 daltons for obtaining a desalted elution fraction and lyophilizing said desalted elution fraction into the sought, delipidated, enriched lipase extract, or e)2 subjecting the buffered solution of pH between 2 and 7 obtained under d) hereinbefore to chromatography on a molecular sieve, collecting a retained elution fraction corresponding to molecular weights between 30,000 and 55,000 daltson and containing the delipidated, enriched lipase extract, filtering said retained elution fraction corresponding to molecular weights between 30,000 and 55,000 and containing the enriched lipase extract on a membrane having a cutoff threshold between 5,000 and 10,000 daltons for obtaining a desalted, delipidated, enriched lipase extract solution and lyophilizing said desalted, delipidated, enriched lipase extract solution into the sought, delipidated, enriched lipase extract;

f) for obtaining the lipase:

f)1 on the basis of the elution fraction having a lipase activity and containing the delipidated, enriched lipase extract obtained in e)1 hereinbefore, subjecting it to chromatography on a molecular sieve, collecting a retained elution fraction corresponding to molecular weights between 45,000 and 50,000 daltons and containing the lipase, filtering said elution fraction containing the lipase on a membrane having a cutoff threshold of 5,000 to 10,000 daltons for obtaining a desalted solution containing the lipase and lyophilizing said desalted solution containing the lipase, or f)2 on the basis of the retained elution fraction corresponding to molecular weights between 30,000 and 55,000 daltons and containing the delipidated, enriched lipase extract obtained in e)2 hereinbefore, adsorbing it on an ion exchange support, desorbing the support by an eluent, whereof the ionic strength is progressively increased as a function of time, collecting an elution fraction having a lipase activity and containing the lipase, filtering the elution fraction having a lipase activity and containing the lipase on a membrane having a cutoff threshold of 5,000 to 10,000 daltons for obtaining a desalted elution fraction containing the lipase and lyophilizing said desalted elution fraction containing the lipase into the sought lipase.

In the present context, the term "delipidated" is understood to mean a product containing the lipase according to the invention, with the exclusion of lipids. Essentially the process comprises an extraction method A making it possible to obtain extracts with a specific lipase activity between 1 and 100 units per milligram of protein and a separation method B which, on the basis of the aforementioned extracts, makes it possible to obtain enriched lipase fractions having a specific activity exceeding 100 units per milligram of protein and also, as the ultimate purification stage, a pure lipase, whose specific activity is close to 1,000 units per mg of protein. Methods A and B of the process, as well as the optional preparation stages of the organs are described hereinafter.

The inventive process makes use of adult rabbits, i.e. rabbits aged more than at least one month and preferably at least two months. These adult sized rabbits are intended for human food and the removal of their stomachs does not decrease their commercial value. The invention does not make use of the stomach of the weaned or unweaned young rabbit, which is known to have a lipase activity with a pH maximum differing from that of the lipase according to the invention and which would lead to unsurmountable cost problems, both due to the small size of the rabbit's stomach and the impossibility of selling the remainder of the sacrificed rabbit.

In the same way, use is only made of the stomachs of adult horses aged in particular at least one year and preferably at least three years.

It has been found that, in the rabbit, the sought lipase is exclusively found in the fundus of the stomach, which is the upper part thereof continued in the lower part of the antrum. It has also been found that the lipase is only encountered in the upper part of the greater curvature of the fundus. It is therefore possible to treat the entire rabbit stomach or any fraction thereof covering the upper part of the greater curvature. The same applies with regards to the horse, the lipase being encountered solely in the fundus. As the fundus is a projecting part of the stomach it is very easy to cut it from the remainder, which facilitates the collection, storage and transportation operations.

This preparation of the organs is optional and can comprise the preparation of the stomachs, the selection and fragmentation of the tissues and delipidation operations. The choice of these treatments is decided on the basis of the state and nature of the available organs, as well as the quality and in particular purity of the desired lipase product. For example, the following diagram summarizes the preferred procedure and the succession of the preliminary operation.

The preliminary operations firstly consist of eliminating from the stomachs removed in the abattoir, possible impurities and contaminants, as well as parts of adjacent organs (esophagus, intestine, spleen) and then optionally separating and eliminating the antrum. The tissues can possibly be frozen and kept at $-20°$ C. prior to fragmentation. The latter can take place manually or with the aid of an apparatus making it possible to obtain irregular fragments, whose maximum size is equal to or less than 5 cm.

The performance of the delipidation stages consists of homogenizing the tissues or solid extracts obtained during the processes of the invention by grinding or extraction with the aid of a hydrophilic solvent with a low boiling point, such as low molecular weight ketones and alcohols. In certain cases, acetone is the most widely used solvent and permits both a possible dehydration and a partial delipidation of the treated product.

The homogenization operations and all the operations performed during the preparation of the products according to the invention are performed at temperatures below $25°$ C. and preferably below $10°$ C., in order to best prevent denaturation of the active principles. These irreversible denaturations can be of a chemical or physicochemical nature, as a function of the extraction conditions and the nature of the solvent used.

Generally, for homogenizing the organs by grinding, use is made of 1 to 10 parts of solvent for 1 part by weight of the product to be treated. Grinding takes place at a temperature below $25°$ C. in efficient equipment of the "Warring blender" type in order to obtain a dispersion of tissue particles of size less than 2 mm. Using this apparatus, this result is obtained after grinding for between 30 seconds and 5 minutes at speeds of 10,000 to 30,000 rpm.

The insoluble fraction is separated by decanting, filtering or centrifuging. Use is normally made of filtration under an industrial vacuum of approximately 50 millibars. In this case, the pulverulent insoluble matter obtained is delipidated and has a homogeneous constitution and can either be directly used in extraction method A, or, following the elimination of the residual solvent under a vacuum of approximately 20 millibars and a temperature of $25°$ C., can be used in more marked delipidation operations or can optionally be used as a partly delipidated lipase extract obtained by the inventive process.

These operations consist of bringing the products to the desired delipidation level by treating them with solvents able to solubilize the fatty matter, such as hydrocarbons, ethers, ketones, alcohols or carbon halides, which can be used singly or in mixtures. These solvents must be easily eliminatable and their boiling point is close to or below $80°$ C. For example, they are pentanes, hexanes, petroleum ethers, diethylether, tetrahydrofuran, chloroform, methylene chloride, carbon tetrachloride and dichloroethane.

The delipidation operations can comprise for the same treatment several successive extractions with the same or different solvents up to the obtaining of an adequately delipidated product.

The lipid content of the solid lipase extracts of the products prepared according to the invention is determined by a variant of the aforementioned method. After drying a sample of the product at $100°$ to $105°$ C. for 6 hours, the lipids are extracted by a methanol:- chloroform mixture (25:75 v/v) for 3 hours at ambient temperature. The insoluble material is filtered and the solvents are eliminated by evaporation. The weight of the evaporation residue obtained related to the weight of the initial sample makes it possible to determine the lipid content, which is generally below 1% for delipidated extracts.

This delipidation level is determined in accordance with the forms provided for the end product, which can e.g. be tabletted or pulverulent and can be realized with products according to the invention having different organoleptic qualities. The delipidation level can be estimated by determining in a prior test, all the hot-extractable fatty substances and then by determining cold for each delipidation treatment the quantity extracted on an aliquot fraction of the liquid phase.

The operation in itself consists of intimately mixing in an appropriate apparatus 1 part by weight of the material to be treated with 5 to 100 parts of the chosen delipidation solvent, for a period of 15 seconds to 15 minutes and at a temperature below 25° C. The delipidated product is separated from the solvent by filtration or centrifuging and can be retreated in an identical way for the number of times necessary for obtaining a desired degree of delipidation.

Thus, more specifically and using the preferred solvents which are acetone, ether, chloroform and mixtures thereof, to 1 part by weight of the product to be treated are added 5 to 25 parts by volume of solvent, followed by vigorous stirring for between 30 seconds and 10 minutes and at a temperature between 0° and 10° C. The delipidated or partly delipidated insoluble matter is separated by vacuum filtration. In the case of incomplete delipidation, the insoluble matter is retreated in the same way. In order to arrive at the desired degree of delipidation, the operation can be repeated 2 to 5 times.

As stated hereinbefore, separation method A is essential for preparing the products according to the invention, whose specific lipase activity is between 1 and 100 units/mg of protein. This method A consists of treating in an aqueous acid medium the stomachs, as such or after being optionally prepared in accordance with the aforementioned operations. Thus, it is possible to use whole stomachs, or selected parts thereof, or even the pulverulent material obtained after homogenization by grinding in a solvent, such as acetone or the same material in delipidated form. The second operation consists of salting out lipase products brought about by the addition of hydrosoluble salts.

More precisely, the extraction operation in acid aqueous media consists of very vigorously stirring the materials with appropriate acid solutions and then separating the liquid phase containing the active principles by filtering, centrifuging or optionally decantation. Thus, conventionally, for 1 gram of material, use is made of 1 to 100 milliliters of acid solution, whose pH is adjusted from 2 to 4.

The acidity of the aqueous phase is brought about by acids having an appropriate strength to obtain such pH values. Use is made of strong mineral acids or organic acids, whose pKa is below 5. These are essentially oxalic, tartaric, malic, citric, maleic, formic, lactic and acetic acids, or also sulphuric, phosphoric and hydrochloric acids, which are those most widely used.

In the case where this operation is performed on tissue fragments, the addition of proteases, such as e.g. pepsins can improve the extraction of the lipase in acid aqueous media.

The operation conditions are adapted to prevent irreversible denaturation of the sensitive active principles, particularly at temperatures above 25° C. In general, the extractions are carried out by energetic mixing of the constituents for between 1 minute and 15 hours, as a function of the efficiency of the mixer used and at a temperature between 0° and 20° C.

In preferred manner, for 1 g of material to be treated, use is made of 3 to 60 milliliters of hydrochloric acid solution with a pH adjusted to 2 to $4\pm 0.1$; said solutions being e.g. obtained for pH 2 by adding 2.0 ml of 37% hydrochloric acid in 2 liters of water.

The thus obtained mixture is homogenized under violent stirring for 5 to 60 minutes and at a temperature between 0° and 20° C. The aqueous phase is then separated by filtration, decantation or centrifuging. In the latter case, the most appropriate conditions consist of performing centrifuging for between 15 minutes and 1 hour at speeds of 3,000 to 12,000 rpm and at temperatures of 4° to 20° C. Separation can also take place by filtration and in this case, the operation is advantageously accelerated by using vacuum or pressure filtration systems.

Thus, the mixture can be concentrated by ultra filtration, frozen and lyophilized in order to obtain the extract in solid form, whereby the latter can optionally be delipidated by the previously described operations.

In this case, the mixture is firstly frozen by cooling to $-20°$ to $-70°$ C., said temperatures being ensured by water-glycol mixtures or solid carbon dioxide-acetone mixtures for the lowest temperatures. These operations are carried out in containers adapted to the following lyophilization operation equipment. Lyophilization is performed under a vacuum below $10^{-1}$ millibar. The water eliminated by sublimation is condensed by traps at a temperature below $-50°$ C. and in particular $-80°$ C. cooled with ammonia or freon. The amorphous dehydrated product obtained is then cold pulverized, such as e.g. by cryogrinding at a temperature below 0° C. prior to being delipidated and then extracted according to method A. All the lyophilizing operations according to the invention are performed in the same way.

The second operation of method A consists of precipitating the lipase activity substances contained in the acid aqueous solutions obtained during the preceding operation. This precipitation is carried out by salting out, which consists of adding to the solution hydrosoluble salts. As cations, these salts contain magnesium, potassium, sodium, ammonium and, as anions, acetate, citrate, phosphate and sulphate. However, the preferred salts are combinations of polyvalent anions and in particular phosphate and sulphate. Alkaline earth cations such as calcium and barium, which cause irreversible denaturations of the proteins are to be proscribed. The preferred salt is ammonium sulphate.

In this case, for 1 liter of acid solution to be treated, accompanied by stirring and at a temperature between 0° and 20° C., are added 80 to 700 g of crystalline ammonium sulphate. Stirring is maintained until the salt has substantially entirely dissolved. The mixture is then left at between 0° and 20° C., so as to bring about a maximum salting out of the active substances, which takes 15 minutes to 20 hours. The solution is then eliminated by conventional means, such as decanting, filtering or centrifuging.

In a particularly preferred manner, this salting out operation is carried out by adding at a temperature between 0° and 10° C., 100 to 600 g of ammonium sulphate for each liter of acid solution to be treated. The solution left at approximately 10° C. for between 30 and 60 minutes leads to the deposition of an optimum quantity of insoluble material with a lipase activity, which is separated by filtration under a vacuum of approximately 50 millibars or by centrifuging for 10 to 45 minutes at a speed of 3,000 to 10,000 rpm and a temperature between 4° and 10° C. The thus obtained product contains the active substances, other biological substances and various mineral salts, including those introduced during the treatments.

As such, it can be used in industrial operations. However, for pharmaceutical operations, it is necessary to eliminate salts, which is brought about by membrane filtration (dialysis or ultra filtration), the latter method being more particularly used. After redissolving the insoluble matter in water, it comprises subjecting the solution to ultra filtration, whilst maintaining the product at a constant volume by adding water to a membrane, whose texture permeable to low molecular weight molecules retains the products and in particular the higher molecular weight enzymes.

Thus, the insoluble matter obtained by salting out is dissolved in water, the pH of the solution is adjusted between 2 and 7 by adding dilute hydrochloric acid and the acid solution is ultra filtered by tangential circulation on a membrane generally having a cutoff selectivity of 5,000 to 10,000 daltons for desalting purposes. All the desalting operations take place in the same way according to the inventive process.

During filtration, the constant flowrate is kept as fast as possible, which is ensured by using a peristaltic pump. However, the pressure of the fluid on the membrane is controlled and must not exceed 1 bar, so as not to cause clogging. Under these conditions, a 200 cm$^2$ membrane makes it possible to treat 2 to 3 liters of filtrate per hour.

After filtration, the retained matter obtained containing the substances having a higher molecular weight than that of the cutoff selectivity of the membrane will be concentrated 2 to 5 times by ultra filtration on the previously described apparatus prior to freezing and lyophilization under a high vacuum of approximately $10^2$ millibar, according to the already defined methods and operating conditions.

These operations make it possible to obtain as inventive products, extracts having a lipase activity characterized by a specific activity of 1 to 100 units/mg of protein.

Using method B, these extracts make it possible to obtain, by appropriate methods, enriched extracts and pure lipase fraction, which are also products according to the invention.

This method can have two purification operations consisting of ion exchange chromatography utilizing the ionization capacity of certain functions of organic compounds and gel filtration which, with the aid of an appropriate support, makes it possible to separate compounds of different molecular weights and sizes. In the case where the preceding operations have not included the delipidation stage, gel filtration is preferred.

When the lipase extract has been delipidated in a preceding stage, the performance of one or other of these operations makes it possible to obtain enriched lipase extracts and in this case ion exchange chromatography is preferred.

Obtaining the lipase requires the successive performance of both operations, which can be performed in random order.

These purification methods will now be summarized. Ion exchange chromatography relates to the purification of hydrosoluble substances incorporating ionizable functions which, in appropriate media, can acquire positive and negative charges permitting the fixing thereof to oppositely charged supports. The elution of products fixed to the support takes place progressively as a function of their bonding force and consequently in certain cases makes it possible to separate products from mixtures.

Thus, enzymes with protein structures carry both amino functions and carboxyl functions with together a zero charge at the isoelectric pH of the molecule. An acidification of the solutions below said pH acts on the carboxyl functions and positively charges the enzyme, whereas conversely an alkalinization acts on the amino functions and leads to a negative charge of the product.

These amphoteric properties of the proteins permit their purification by cation or anion exchange chromatographic methods.

The supports used for such methods are substances which are insoluble in the elution medium used and incorporating ionizable functions.

The main types of support are resins, three dimensional styrene and polyvinylbenzene systems, substituted celluloses, dextran derivatives or agarose derivatives. Among the latter, the firm Pharmacia proposes a highly crosslinked agarose polymer support permitting particularly fast separations (Fast Flow trademark).

In their structures, these different supports have ionizable functions, such as sulphonic, carboxylic, phosphoric and arsenic functions for cation exchanges and primary, secondary or tertiary amine functions for anion exchanges.

In preferred manner, the products according to the invention have been purified by cation exchange chromatography on columns of the Fast Flow S and Sepharose types (Pharmacia) of dimensions diameter 2.6 mm and height 30 cm, whose supports carry sulphopropyl radicals and which are consequently cation exchangers, or on columns containing an identical support, but having a lower capacity (1 ml) of the Fast Flow mono S type (Pharmacia).

The extracts to be purified are dissolved in buffers with a pH between 3 and 5 and in particular 4. Buffer examples are given below.

|  |  |  |
|---|---|---|
| a) | Sodium acetate | 20 mM/liter |
|  | Sodium chloride | 100 mM/liter |
|  | Acetic acid ad | pH 4 |
| b) | Sodium acetate | 20 mM/liter |
|  | Acetic acid ad | pH 4 |

The solutions of extracts are deposited on gels previously balanced with the buffer used for the purification. The latter differs as a function of the type of column used.

In the case of "mono S" type columns the extract is solubilized in buffer b). The products are purified by the same buffer progressively enriched with a buffer of a different type, but containing 500 mM of sodium chloride per liter, in order to obtain an elution gradient of pH 4 progressively containing 0 to 500 mM of sodium chloride per liter. The progressive modification of the ionic strength makes it possible to separate, for a concentration of approximately 250 mM per liter of sodium chloride, a fraction containing the enriched lipase extract.

With "S Sepharose" type columns, the product to be purified is dissolved in buffer a) and deposited on the column. Elution takes place with the same buffer and then with a solution consisting of 20 mM/liter of sodium acetate and 200 mM/liter of sodium chloride, which makes it possible to elute a lipase fraction enriched with the sought extract.

This purification method applied to the extract obtained in method a) following salting out makes it possible to obtain fractions containing the enriched lipase extract, whose specific activity is between 100 and 500 units per milligram of protein.

The aqueous fractions obtained by these purifications can either be used in a complementary purification method for obtaining the lipase, or can be desalted by dialysis or ultra filtration, then frozen and lyophilized by the already described methods in order to obtain an enriched lipase extract in amorphous solid form.

The filtration on gel of the "molecular sieve" type permits a separation of the molecules as a function of their size, i.e. their volume or dimensions. The insoluble gels used are formed from variable 3-dimensional systems accessible to an adapted molecule size.

Thus, with a mixture of molecules of different sizes, only the products of a size adapted to the system of the gel will be retained, whereas the molecules of a greater size will not be retained and will be rapidly eluted. For molecules retained on the gel, their retention time is also dependent on their size and the elution of these products takes place in an order proportional thereto, the smaller molecules being held back more.

The following gels have these separating properties:

Sephadex G, constituted by dextrans bridged with epichlorohydrin,

Biogels P, which are polyacrylamide chains bridged by N, N'-methylene bisacrylamide, Ultrogels and Sephacryls, which combine a mixed polyacrylamide and agarose grid.

The products of the present invention were preferably treated with polyacrylamide gels of the Sephacryl type.

The non-delipidated extracts are treated by a sieve, whose exlusion limit exceeds 1,000,000 daltons.

Thus, the aqueous solutions of the products to be purified are deposited on a column with a height of approximately 1 meter and containing 1 to 7 liters of gel.

Elution is then carried out by a pH 6 solution containing 100 to 500 mM of sodium chloride and 10 to 30 mM of disodium phosphate. The eluate is collected by fractions and the lipase activity is investigated in these fractions. Thus, the fractions containing the activity are desalted by dialysis or ultra filtration, followed by freezing and lyophilization in order to obtain the sought enriched lipase extract in solid form.

The delipidated lipase extracts are treated with a sieve permitting the separation of substances with a molecular weight between 30,000 and 55,000 daltons and particularly 45,000 and 55,000 daltons. Thus, the aqueous solutions of the products to be purified are deposited on a column with a height of approximately 1 meter and containing 400 to 500 ml of gel.

The elution is then carried out by a pH 6 solution containing 200 mM/liter of sodium chloride. The eluate is collected in fractions and the lipase activity is sought in these fractions.

Obtained in this way, the fractions containing the lipase activity can either be used in a complementary purification method for obtaining the lipase, or can be desalted by dialysis or ultra filtration, then frozen and lyophilized in order to obtain an enriched lipase extract in solid form and which in certain cases can undergo delipidation.

The process according to the invention has been applied to the stomachs of calves, sheep, pigs, poultry, rabbits and horses. However, in a surprising manner and contrary e.g. to what is obtained when starting from pig stomachs, the lipase substances and lipases obtained from the stomachs of rabbits and horses have a maximum lipase activity at a pH between 4 and 5 and particularly at 4.5, whereas it is 6 to 7 for the pig and is consequently not very active in a gastric medium.

Moreover and unexpectedly, it has also been found that, contrary to the extract obtained from pig stomachs, the rabbit and horse stomach extracts retained their lipase activity following incubation in an acid medium. Incubated for 2 hours at 37° C. and a pH of 2, these activities are not deteriorated, whereas those of pig stomachs treated in the same way are unable to resist a pH below 4.

Moreover, the activities of the extracts of the horse and pig stomachs were investigated in a pH range of 3 to 9. Between pH 3 and 7, for the extracts there was a lipase activity equal to or greater than 50% of that of their maximum activity occurring at approximately pH 4.5. The test protocols are described in the subsequent text.

Thus, the remarkable properties of resistance to denaturation in the acid medium, as well as the wide activity range of lipases of rabbit and horse stomach extracts justify their use in medicament form as a substitute for lipase activities in various cases of pathological deficiency in man and animals.

The invention therefore relates to a lipase having a molecular weight according to the Laemmli method of 49,000 daltons, whereof 9,000 correspond to sugars and 40,000 to a protein, the number of amino acid types being as follows: Asp. Asn: 45: Thr: 19: Ser: 28: Glx: 30: Pro: 29: Gly: 25: Ala: 28: Val: 27: Met: 8: Ile: 18: Leu: 26: Tyr: 16: Phe: 18: Lys: 17: His: 7: Arg: 10: Cys: 9 and Trp: 6, whereof the N-terminal sequence is: Lys-Ser-Ala-Pro-Thr-Asn-Pro-Glu-Val-Asn-Met-X-Ile-Ser-Glu-Met-Ile-Ser-Tyr-Trp-Gly-Tyr-Pro-Ser-Glü-Lys-Tyr-Glu-Val-Val, X designating an indeterminate amino acid, whose specific lipase activity according to the Gargouri method exceeds 1,000 U/mg of protein, whose maximum activity is obtained for a pH-value of approximately 4.5, whose activity, at pH-values of 3 and 7, is at least equal to half the maximum activity, whose activity is maintained after incubating for 2 hours, at 37° C. and a pH-value of 2, whose amino acid involved in the lipolytic activity is cysteine, which is able to resist pepsin, is degraded by chymotrypsin and by trypsin, whose isoelectric pH is between 5.7 and 7.1 and which can be prepared by the process according to the invention on the basis of rabbit stomach fundus.

The invention also relates to a lipase, whose specific lipase activity according to the Gargouri method exceeds 1,000 U/mg of protein, whose maximum activity is obtained for a pH-value of approximately 4.5, whose activity, at pH-values of 3 and 7, is at least equal to half the maximum activity, whose activity is retained after incubation for 2 hours at 37° C. and at a pH-value of 2 and which can be prepared by the inventive process from horse stomachs.

Finally, the invention is directed at delipidated or non-delipidated, enriched lipase extracts, optionally in aqueous solution, having a specific lipase activity according to the Gargouri method between 100 and 1,000 U/mg of protein, whose maximum activity is obtained for a pH-value of approximately 4.5, whose activity, at pH-values of 3 and 7, is at least equal to half the maximum activity, whose activity is retained after an incubation for 2 hours at 37° C. and at a pH-value of 2 and which can be prepared by the process according to the invention.

The invention is also directed at a delipidated or non-delipidated lipase extract having a lipase activity according to the Gargouri method between 1 and 100 U/mg of protein, whose maximum activity is obtained for a pH-value of approximately 4.5, whose activity, at pH-values of 3 and 7, is at least equal to half the maximum activity, whose activity is maintained after incubation for 2 hours at 37° C. and at a pH-value of 2 and which can be prepared by the process according to the invention.

These pepsin-resistant extracts are degraded by trypsins and have cysteine as the amino acid involved in the lipolytic activity.

These products are characterized and defined by properties conventionally determined for enzymes and enzymatic extracts, namely:
  a—specific activity,
  b—activity as a function of the pH,
  c—resistance of the lipase activity after incubation in acid medium,
  d—determination of the apparent molecular weight,
  e—activity on triglycerides,
  f—determination of the isoelectric pH,
  g—determination of the presence of an essential amino acid involved in the lipolytic activity,
  h—determination of the resistance to proteases,
  i—determination of the presence of sugars.

The methods used for these determinations are summarized hereinafter.

a. The specific activity is defined as being the ratio of the enzymatic activity and the quantity of proteins of the sample expressed in milligrams. The lipase activity is determined by the titrimetric method of Y. Gargouri (Aix-Marseille University PhD thesis, 1985) in which the substrate used is tributyrin. Dosing consists of neutralizing the butyric acid freed under the action of the lipase by a 0.1N sodium hydroxide solution at a constant pH of 6 and a temperature of 37° C. Under these test conditions, the enzymatic activity corresponds to the number of micromoles of acid freed in 1 minute by the action of the product undergoing the test.

In practice, the test consists of introducing into a titration cell thermostatically controlled to 37° C. 0.50 ml of tributyrin and 14.50 ml of sodium taurodesoxycholate and serum bovine albumin isotonic solution (composition: 100 mg of serum bovine albumin, 2 mM sodium taurodesoxycholate, 9% Nacl isotonic solute, ad 1 liter).

Under electromagnetic stirring or agitation and using an automatic titrimeter, the mixture is brought to pH 6 by adding 0.1N sodium hydroxide. After stabilizing the pH at this value, in accurately measured manner are added 0.5 to 1 ml of an aqueous solution of the enzymatic compound to be dosed. Under these experimental conditions, the 0.1N sodium hydroxide solution quantity necessary for maintaining the pH at 6 for 2 minutes makes it possible to calculate the lipase activity, as defined hereinbefore.

The proteins are determined in the presence of a Folin Ciocalteu reagent. In the presence of cupric ions in an alkaline medium and said phospho-molybdo-tungstic reagent, a coloured complex is formed having an intensity proportional to the protein quantity (Lowry et al, 1951). The colouring is compared with that of a standard range prepared with known serum bovine albumin quantities, so that in this way it is possible to determine the protein concentration of the sample to be tested.

b. The activity as a function of the pH is determined in a pH range of 3 to 9 using an adaptation of the previously described dosing method. Thus, the titration mixture is brought to the chosen pH-value for the study, either by adding a 0.1N sodium hydroxide solution, or by adding a 0.1N hydrochloric acid solution. The enzymatic solution is added and the pH is maintained at this pH-value for 2 hours.

The dissociation coefficient of butyric acid (pka=4.75) authorizes direct dosings at pH 6, dosings with a corrective factor up to pH 5 and so-called "return" dosings for values below this pH.

c. Resistance of the lipase activity after incubation in an acid medium. This study consists of determining the lipase activity after subjecting the test product to incubation for max 2 hours and at 37° C. in aqueous solutions with pH-values between 3 and 9.

An aqueous solution of the enzymatic extract to be studied is brought to different pH-values by adding 0.1N hydrochloric acid or sodium hydroxide solutions. These solutions are placed in a bath thermostatically controlled at 37° C. Samples are taken at 0, 30 minutes, 1 hour and 2 hours and contain tributyrin as the substrate. After rapidly adjusting the pH to 6, the dosing of the lipase activity is performed for 2 minutes by adding 0.1N sodium hydroxide solution to keep the pH-value at 6. The thus determined lipase activity is compared with that of a control sample of the same product which has not been incubated and directly titrated at pH 6 (i.e. the sample at time t=0), which makes it possible to obtain a lipase activity percentage after incubation under the conditions of the experiment.

d. The apparent molecular weight is determined by electrophoresis in accordance with the Laemmli method (Nature, 1970, 227, pp. 680–685), which consists of treating the sample with sodium dodecylsulphate and migration into a polyacrylamide gel successively constituted by a 5% gel and a 12.5% gel (wt/vol). Proteins of known molecular weights between 14,000 and 94,000 daltons are treated identically. Following the visualization of the proteins with Coomassie blue, the apparent molecular weight of the sample is determined by the comparison of its migration with those of the reference proteins. This method makes it possible to obtain a molecular weight of 48,000 daltons for a purified lipase obtained on the basis of rabbit stomachs (example 6).

e. The activities of the lipase or lipase extracts have been studied on 3 substrate types, namely triglycerides with a short chain: tributyrin ($C_4$) with a medium chain: LIPROCILE ($C_8C_{10}$) and with a long chain: INTRALIPIDE, 30% soy oil.

In practice, 2 units are added to 0.5 ml of tributyrin or 0.5 ml of LIPROCILE or 5 ml of a 30% INTRALIPIDE solution and 10 units of lipase activity are incubated in a 9% NaCl buffer, $CaCl_2$ 150 nM and bovine albumin serum.

The study of the activity as a function of the pH shows that the lipase has a maximum activity at approximately pH 5 for tributyrin, a pH of approximately 6 for LIPROCILE and a pH of 4 for INTRALIPIDE.

The activity of the lipase products obtained is determined at pH 5 on the previously listed substrates. The activities found on LIPROCILE and INTRALIPIDE are respectively between 50 and 75% and 25 and 40% of that observed on tributyrin.

f. Determination of the Isoelectric pH

The proteins placed in an electric field and in a pH gradient formed by ampholytes migrate up to their isoelectric pH. The gradient is formed by a mixture of polyelectrolytes with a molecular weight equal to or below 1,000, constituted by polycarboxylic and polyamino aliphatic acids having isoelectric points between 2 and 11.

2 to 5 μg of lipase extract are deposited on a preformed horizontal gel and the proteins subjected to an electric field migrate for approximately 1 hour. The presence of bands is visualized by the silver nitrate reagent. The pH of the lipase is between 5.7 and 7.1. The presence of several bands in this pH field is due to a heterogeneity of the sugar chains bonded to the protein.

g. Determination of the Presence of an Essential Amino Acid in the Lipolytic Activity This study consists of adding to the lipase or lipase extracts, a reagent having the property of blocking the activity of the enzyme. The reagents used by us are DNTB (5,5'-dithio-bis-2-nitrobenzoic acid) and 4 PDS (4,4'-dithiopyridine) which, in certain pH conditions, are fixed to the free sulphydric groups of the protein. Following fixing, these reagents free the following coloured groups:

DNTB frees 5-thio-3-nitrobenzoic acid, which can be dosed at a wavelength of 420 nm;

4 PDS frees the 4-thiopyridone group, which can be observed and quantified at the wavelength of 324 nm.

Thus, in a 1 millilitre spectrophotometric cell, incubation takes place in a pH 8 buffer of tris HCl 0.25M the acid lipase and the reagent in excess. At different times, the absorption of the freed compound is measured and its concentration calculated with the aid of its molar extinction coefficient:

(E $1_{cm}$, M=13 600 at 420 nM)
(E $1_{cm}$, M=19 800 at 324 nM)

at the same time, a sample is taken and makes it possible to measure the residual lipolytic activity with the method described in a. The lipase activity of the purified lipase is consequently totally inhibited by these reagents. Moreover, the calculation makes it possible to determine that a single free sulphhydryl group participates in the lipolytic activity, said group belonging to the amino acid cysteine. The lipase extracts treated under the same conditions are also inhibited.

h. Determination of the Resistance to Proteases

This research was carried out with pig pepsin, this enzyme being secreted in the stomach, chymotrypsin and trypsin of pigs, said enzymes being secreted in the duodenum by the pancreas.

The lipase extracts and lipase are incubated for 2 hours at pH 7.5 for chymotrypsin and trypsin and at pH 2 for pepsin at 37° C. Samples are regularly taken every 15 minutes and the residual lipase activity is determined by the method described in a.

Thus, 2 mg of pepsin are brought together with 3 mg of lipase or lipase extract in a pH 2 buffer. In the same way, 2 mg of trypsin or chymotrypsin are brought together with 3 mg of lipase or lipase extracts in a pH 7 buffer. The activity used as a reference was determined in c.

The initial activity remains unchanged for 2 hours with pepsin. At the end of 2 hours, the activity in the presence of chymotrypsin is reduced by 50% and trypsin has completely destroyed the lipase activity in 2 hours.

i. Determination of the Presence of Sugars

This study consists of hydrolyzing the sugar chains bonded to the protein by a specific endoglycosidase, ENDOF, the enzyme which intersects between two N-acetylglucosamines.

The method consists of determining the apparent molecular weight of the product obtained from the lipase treated by this enzyme. After hydrolysis and treatment in accordance with the method described in d, there is a major intensity band corresponding to a molecular weight below that obtained from the native enzyme and close to 40,000 daltons. Moreover, the amino acid composition makes it possible, on the basis of the weight of each amino acid, to determine a weight of the protein of approximately 40,000. The difference with the weight determined by the Laemmli method described in d is approximately 9,000 daltons and corresponds to the sugar fraction of the enzyme.

The purified lipase made it possible to determine the biochemical characteristics of the lipase, namely the amino acid composition and the N-terminal sequence.

The amino acid composition was determined after hydrolysis of the protein by hydrochloric acid at 24, 38 and 72 hours. The hydrolysates were then analyzed according to the method of D. H. Spackmann, W. H. Stein and S. Moore (Anal. Chem., 1957, 228, p. 999) with an automatic amino acid analyzer (Spinco-Beckman), the analytical results then being dealt with by the method of M. Delaāge (Biochem. Biophys. Acta, 1968, 168, p. 573).

The cysteine residues are determined by performic oxidation and the tryptophans by hydrolysis in the presence of mercapto ethanesulphonic acid according to the method of B. Penke, R. Ferenzi and K. Fouacs (Analytical Biochemistry, 1974, 60, pp. 45–50).

The number of the different amino acid types determined is as follows: Asp. Asn-45; Thr-19; Ser-28; Glx-30; Pro-29; Gly-25; Ala-28; Val-27; Met-8; Ile-18; Leu-26; Tyr-16; Phe-18; Lys-17; His-7; Arg-10; Cys-9; Trp-6.

The N-terminal sequence of the protein was determined according to the method of Fred. S. Esch (Anal. Biochem., 1984, 136, pp. 39–47). The terminal sequence of 30 amino acids is as follows: Lys-Ser-Ala-Pro-Thr-Asn-Pro-Glu-Val-Asn-Met-X-Ile-Ser-Glu-Met-Ile-Ser-Tyr-Trp-Gly-Tyr-Pro-Ser-Glu-Lys-Tyr-Glu-Val-Val. (X: undetermined).

The invention finally aims at a medicament for combating malabsorptions of fatty materials in man and animals, which has as the active principle a lipase and/or a lipase extract according to the invention.

The following examples illustrate the invention.

EXAMPLE 1

Non-Delipidated Lipase Extract Prepared According to Method A

The stomachs of rabbits aged 2 to 3 months are collected from the abattoir. The upper third of the fundus is cut open and its content emptied. The tissues are frozen at −20° C. and then fragmented into portions smaller than 2 cm.

Homogenization and Extraction in an Acid Medium According to Method A 160 g of fragmented tissues are added to 600 ml of hydrochloric solution at pH 2.5, a temperature of 10° to 12° C. and containing 0.06% wt/wt of pepsin. Homogenization is carried out at a temperature close to 20° C. by stirring the mixture for 45 minutes at approximately 900 rpm using a helical stirrer.

Insoluble matter is separated by centrifuging at 5000 rpm for 30 minutes. The pale yellow supernatant acid phase is separated:
volume: 540 ml
total activity: 175,000 units

Ammonium Sulphate Precipitation

Accompanied by stirring and at a temperature of 12° C., 147 g of ammonium sulphate are slowly added to the acid solution obtained during the preceding operation. Following addition, the solution is left for 15 minutes at 15° C. The salted out precipitate is separated by centrifuging at 3,500 rpm for 20 minutes.

The bottom containing the enzyme fraction is dissolved in 175 ml of phosphate buffer at pH 6. A pale yellow, clear solution is obtained, which contains a few mechanical impurities.
volume: 175 ml
total activity: 124,250 units

EXAMPLE 2

Non-Delipidated, Enriched Lipase Extract Prepared According to Method B

The preceding solution is filtered on filters with a porosity of 5 μn.

The thus obtained solution is purified by chromatography on Sephacryl S 300 gel supplied by Pharmacia (height 1 meter, volume 7.5 liters), whilst eluting with the already described buffer at pH 6 and at a flowrate of 115 ml/h. The presence of the sought lipase activity is detected as from the first collected fractions. These fractions are collected to obtain a homogeneous fraction.
volume: 830 ml
total lipase activity: 100,642 units This concentrated, lyophilized, desalted solution makes it possible to obtain 317 grams of pale yellow, amorphous powder of non-delipidated extract with an enzyme acitivity of 98,000 units and a specific activity of 31 units per mg of powder.

Activity at different pH-values
pH 3: 4,503 u
pH 5: 8,750 u
pH 7: 4,412 u

Resistance to acid pH-values
pH 2
at time: 0, 8,300 units
at time: 2 hours, 8,000 units Activities on Triglycerides with the Following Chains:
short: 8,750 units
medium: 6,829 units
long: 3,233 units Inhibition of Activity by Specific Reagents of Cysteines Complete inhibition of the lipase activity at pH 8 by the reagent DNTB.

Action of Proteases

Degradation:
zero by pepsin,
between 40 and 50% by chymotrypsin,
complete inhibition by trypsin under the aforementioned operating conditions.

EXAMPLE 3

Delipidated Lipase Extract Prepared According to Method A a. Preparation

The gastric parts of the viscera of rabbits of the Janny species or the country species and aged between 2 and 3 months are collected from the abattoir. The stomachs are prepared by eliminating any impurities, as well as portions of the esophagus, intestine and spleen.

Homogenization, Dehydration and Delipidation 225 g of tissues are ground at 5° C. in 2,250 ml of acetone in a flame/explosion-proof apparatus for 30 seconds and at 30,000 rpm. The insoluble matter is vacuum filtered on a Büchner filter and washed with 100 ml of cold acetone. The insoluble matter is taken up and the operation repeated under the same conditions with, successively, the following delipidation solvents: acetone (3 times), chloroform (3 times) and diethyl ether (3 times).

The powder is finally dried in vacuo in a desiccator to constant weight: weight 45 g.

b. Method A

Acid Aqueous Extraction

The delipidated powder is introduced into 1,125 ml of hydrochloric solution of pH 2.5 and previously cooled to 5° C. The mixture is stirred at 4° C. for 30 minutes and then the insoluble fraction separated by centrifuging at 10,000 rpm for 30 minutes. The aqueous phase is separated.
volume: 1,125 ml
specific lipase activity: 7 U/mg of protein
total lipase activity: 75,000 U Activity unchanged after incubation for 2 hours at 37° C. and pH 2.

Ammonium Sulphate Precipitation

Accompanied by stirring and at a temperature of 4° C. gradual addition takes place of 352 g of ammonium sulphate to the acid solution obtained during the preceding operation. After addition, the mixture is left for 30 minutes at the same temperature and then centrifuged at 10,000 rpm for 30 minutes.

The supernatant material is decanted and the centrifuging bottom containing the enzyme fraction is dissolved in 300 ml of water. The enzymatic characteristics of the solution are determined:
specific lipase activity: 73 U/mg of protein total lipase activity: 37,500 U This solution is directly used for purification according to method B in example 4, having previously undergone the following treatment. The ammonium sulphate contained in the solution is eliminated by dialysis at 4° C. and accompanied by stirring being replaced by 15 liters of buffer solution at pH 4 (20 mM/l sodium acetate, 100 mM/l sodium chloride and acetic acid ad pH 4). One hour afterwards the buffer is eliminated and the operation repeated twice, whilst renewing the buffer solution. Finally 300 ml of lipase activity solution are obtained, in which the ammonium sulphate is eliminated. This solution is purified as described in the following example.

EXAMPLE 4

Enriched Lipase Extract Prepared According to Method B: Ion Exchange Chromatography Purification is performed on a Fast Flow S Sepharose column (supplied by Pharmacia) containing 60 ml of gel with a diameter of 26 mm.

The column is balanced with the pH 4 buffer solution already used for dialysis, at a flowrate of 100 ml/hour. The 300 ml of solution are then introduced and the elution continued under the same conditions with the pH 4 solution, followed by a second solution comprising 20 mM/l sodium acetate and 200 mM/l sodium chloride at pH 6.5.

After 480 ml of elution, 40 ml of eluate are collected containing the lipase activity with the following characteristics:
specific lipase activity: 350 U/mg of protein
total lipase activity: 28,000 U The solution, which is frozen and then lyophilized, makes it possible to obtain 2.8 g of enriched extract with a specific lipase activity of 10,000 U/gram of product.

EXAMPLE 5

Lipase Extract Prepared According to Method A a. Preparation 50 g of tissue identical to that of example 2 are homogenized, dehydrated and partly delipidated with acetone according to the method given in example 2. After eliminating the residual water and acetone under a vacuum of 40 millibars and at 25° C., 10 g of product are obtained and treated according to method A.

b. Method A

Also applied according to example 2.
Aqueous Acid Extraction
volume obtained: 222 ml
specific lipase activity: 2.6 U/mg of protein
total lipase activity: 8,850 U Ammonium Sulphate Precipitation After centrifuging, the bottom is taken up with 19 ml of buffer solution (150 millimole/liter sodium chloride, pH adjusted to 3 by acetic acid):
specific lipase activity: 17 U/mg of protein
total lipase activity: 6,550 U The solution is used as such in the purification operation described in example 6.

EXAMPLE 6

Pure Lipase Prepared According to Method B

Filtration on Molecular Sieve

The solution obtained in the preceding example is purified on a Sephacryl S 200 gel solution (supplied by Pharmacia) having a diameter of 2.6 cm and a height of 1 m) using for the elution the pH 3 buffer already described at a rate of 16 ml/hour. After 300 ml of eluate, in a volume of 50 ml is obtained the solution containing the purified lipase activity:
specific lipase activity: 257 U/mg of protein
total lipase activity: 4,550 U.

Ion Exchange Chromatography

The operation is carried out on a mono S Fast Flow column (supplied by Pharmacia) with a volume of 0.98 ml. The previously obtained 50 ml of solution are deposited on the column, elution then being carried out at a rate of 1 ml/min using a pH 4 buffer solution (20 mmole/liter sodium acetate comprising a linear sodium chloride gradient between 0 and 500 mmole/liter). The lipase is eluated at a concentration of 250 mmole/liter of sodium chloride in a volume of 20 ml. The product obtained has the following characteristics:
total protein weight: 3.4 mg
specific lipase activity: 1,067 U/mg of protein
total lipase activity: 3,630 U
apparent molecular weight: 48,000
(Laemmli method)
Activity at Different pH-values
pH 3: 100 units
pH 5: 170 units
pH 7: 85 units
Resistance to Acid pH-values
pH 2
at time: 0 150 units
at time: 2 hours 145 units Molecular Weight There is a molecular weight band at 49,000.
Activity on Triglycerides with the Following Chains:
short: 1,200 units
medium: 760 units
long: 300 units Determination of the Isoelectric pH 12 bands between pH 5.7 and 7.1.

Inhibition of Activity by Specific Reagents of Cysteines

DNTB: inhibition in 240 minutes and one molecule of DNTB inhibits one molecule of lipase.
4PDS: inhibition in 60 minutes and one molecule of 4PDS inhibits one molecule of lipase.

Action of Proteases

Degradation
zero by pepsin
between 40 and 50% by chymotrypsin
complete inhibition by trypsin under the previously described operating conditions.

Determination of the Presence of Sugars

Native lipase deposited on an electrophoretic gel has a molecular weight band at 49,000. After incubation with endo F for variable periods of time a band with an intensity rising as a function of time appears with a molecular weight corresponding to 40,000 daltons.

EXAMPLE 7

Lipase Extract Prepared According to Method A

Preparation is carried out on the basis of the gastric mucous membranes of the horse directly using method A.

Acid Aqueous Extraction 228 g of gastric mucous membrane of horse fragmented into approximately 1 cm$^2$ portions are introduced into 910 ml of water cooled to 4° C., the pH of the mixture being adjusted to 2.5±0.1 by adding 37% concentrated hydrochloric acid (wt/v). At 4° C., grinding takes place at 30,000 rpm during two 30 second periods with a 2 minute interval between. The ground material is maintained under cold electromagnetic stirring for 40 minutes and then the acid solution is separated by centrifuging at 10,000 rpm for 30 minutes.

The 892 ml of acid solution contain lipase activity substances at a rate of 15.5 specific units per ml of solution or 0.74 specific units per mg of protein. Total specific lipase activity 13,800 U.

Ammonium Sulphate Precipitation

Under electromagnetic stirring and at 4° C., 500 g of ammonium sulphate are added to the preceding acid solution. Stirring is maintained for 30 minutes at this temperature and then the insoluble matter is separated by centrifuging at 10,000 rpm for 30 minutes. The bottom is taken up by 50 ml of 9% sodium chloride solution and the mixture is again centrifuged under the same conditions.

The supernatant material contains the enriched lipase activity:
volume: 51 ml
specific lipase activity: 192 U/ml-5.6 U/mg of protein
total lipase activity: 9,800 U This solution can be treated according to the already described procedures to obtain a solid product.

EXAMPLE 8

Rabbit stomachs identical to those used in example 1 are employed. The antrum (part A) is separated from the fundus (part B). The fundus is itself segmented into four equal parts cut in the widthwise direction of the organ ($B_1$, $B_2$, $B_3$, $B_4$ classified as from the antrum). These different tissues are treated identically to that of example 1. The lipase activities obtained in each acid extract are determined by the Gargouri method and the following results are obtained:

A=0
$B_1$=0
$B_2$=0
$B_3$=0
$B_4$=6,000 units

The lipase activity is located in the upper part of the fundus.

Independently of an absence of toxicity in the animal, the products according to the invention have favourable effects on pathological disorders of the digestion in man.

The toxicity investigation was carried out on 7 to 8 week old Wistar rats, to which was orally administered an aqueous solution saturated in lipase extract obtained from rabbit stomachs at a rate of 1 ml containing 50 lipase units for 100 g of animal body weight and this was administered daily for 4 weeks.

At the end of the treatment, the following examinations recommended by Organization for Economic Cooperation and Development were carried out: on the living animal haematological, biochemical, blood and urinary examinations and on the dead animal histopathological examinations.

Compared with the untreated controls, no abnormality was observed in the animals which had received the lipase extract. These studies and the perfect tolerance of the animals during the treatment demonstrate the absence of toxicity and the harmlessness of the product.

The effectiveness of the products according to the invention, either alone or associated with other enzymes used in human digestive pathology was also demonstrated.

Products in the form of powder or capsules have been proposed at a rate of 300 to 6,000 lipase units daily, as a function of the gravity of their state, to patients aged 18 to 75 and suffering from established alcoholic chronic pancreatitis. The patients having, prior to treatment, a steatorrhea equal to or greater than 10 g/24 hours, receive the products by ingestion during meals or mixed with their food for 6 months.

In most cases, there was found to be reduction in the steatorrhea and a corrective action on the frequency and weight of the stools. In the same way, discomfort symptoms, such as abdominal pains and swelling decreased. Frequently, weight increases were observed. No intolerance was noted during this study representative of the efficacy of the inventive products and this was the case even when compared with other enzymes such as pancreatins, which did not give such a significant improvement effect to the general state of the patients.

Moreover, infants suffering from mucoviscidosis and whose fat absorption coefficient was below 90% were treated for 14 days with product doses comparable to those of the preceding test. During this study, the lipid level in the stools, the weight and the daily number thereof was checked, as was the evaluation of the intensity of the pains and abdominal swellings. There was a marked improvement in the steatorrhea and the general state. Once again the inventive products were more effective than pancreatin.

The inventive products were administered in the form of a medicament with a presentation adapted to the nature and seriousness of the ailment to be treated. Therefore use was made of tablets, gelatin-coated pills, soft capsules, granules, microgranules or pseudo-liquid forms, such as syrups, suspensions and gels.

The lipase extracts can be associated with various substances having an activity on the symptoms associated with the malabsorption phenomenon. It is consequently possible to use gastric protection agents, anti-ulcer agent, anti-gastroesophageal reflux agents and other active enzymes in digestive phenomena.

The above-described medicamentis forms are prepared according to conventional procedures and with the adjuvants currently used in pharmaceutical practice, such as neutral charges permitting the appropriate dilution of the active principle, such as lactose, saccharose, sorbitol, mannitol, starch, cellulose or salts such as phosphates. Use is also made of disintegrating, binding or lubricating products. Optionally, the forms obtained can be sugar coated in order to obtain coated tablets or can be covered in a hydrosoluble film. The function of these coatings is to mask the possibly unpleasant taste of the preparation.

The aforementioned liquid forms, which are particularly useful in paediatrics and geriatrics, advantageously have flavouring and colouring agents added to them giving attractive organoleptic characteristics.

The stability of the various preparations can be ensured by the addition of antioxidants or preservatives, such as tocopherol, ascorbic acid, sorbic acid, its salts, etc.

In order to illustrate medicaments containing the inventive products, the preparation of tablets and powders is described.

TABLETS

Formula for one 180 mg tablet dosed with 1000 lipase units.

Product of example 3 with 73 U/mg of protein. Quantity sufficient for 1000 units, i.e. 100 mg:
corn starch: 22 mg
dicalcium phosphate: 30 mg
microcrystalline cellulose: 15 mg
silica: 12 mg
magnesium stearate: 1 mg

PREPARATION

With the exception of the magnesium stearate, the tablets are intimately mixed, the product obtained is compacted and then calibrated on a grid having a mesh size of 1 mm. The grain obtained is lubricated by adding magnesium stearate and then compressed on a rotary machine at a rate of 180 mg per unit.

POWDER

Formula for 1 g of powder dosed with 400 lipase units per gram.
Product of example 5 with 17 U/mg of protein:
quantity sufficient for 400 units, i.e.: 0.8215 g
ascorbic acid: 0.0025 g
lactose: 0.0760 g
natural orange flavour in powder form: 0.1000 g.

PREPARATION

The constituents are successively introduced into an appropriate stainless steel mixer. After homogenization, the mixture is distributed into brown glass bottles, which are hermetically sealed.

The medicament according to the invention consequently comprises 56 to 82% by weight of the active principle and 44 to 18% by weight of excipient.

As demonstrated hereinbefore, the toxicity of the products according to the invention is insignificant which, as a function of the gravity of the particular case, makes it possible to administer between 300 and up to more than 6000 lipase units daily.

This dose rate is adapted to the age of the patient and in more general cases the daily dose is 600 to 4000 lipase units, which are usually administered three times daily at meals.

The pharmaceutical compositions containing the products according to the invention are particularly appropriate for the treatment of disorders connected with the malabsorption of fatty substances, particularly in the case of pancreatitis of various types, such as alcoholic, hereditary, hypercalcemia or tropical pancreatitis.

They are generally useful in curing sequels to surgery, such as gastrectomy and partial or total resection of the pancreas, which can lead to steatorrhea.

They are also indicated in cases of mucoviscidose and lipase, colipase and enterokinase deficiencies.

The symptoms associated with these ailments are generally steatorrhea, diarrhoea, abdominal pains and denutrition states. Treatment by means of products according to the invention with an appropriate dose rate and duration leads to the regression thereof.

In general terms, compositions containing the inventive products are useful and favourable to assimilation phenomena for alimentary fatty substances. In addition, these products can be administered as a supplement to normal persons, in order to accelerate and/or complete natural assimilation of fats and in the same way accelerate and/or increase their energy supply.

We claim:

1. A process for preparing a lipase extract comprising
    contacting adult rabbit stomach fundus with an acidic aqueous medium having a pH of 1.5 to 5, at a rate of 1 to 10 parts by volume of said acidic aqueous medium per part by weight of said fundus, at a temperature ranging from 4° to 30° C. and for a time ranging from 1 minute to 15 hours so as to obtain a solid material and an aqueous solution containing a lipase portion,
    separating said aqueous solution from said solid material so as to obtain a separate aqueous solution,
    adding to said separate aqueous solution 80-700 g/liter of ammonium sulfate and permitting said sulfate to remain in admixture with said separate aqueous solution for a time sufficient to salt out said lipase extract and to obtain a supernatant solution,
    separating said lipase extract from the supernatant solution, and
    collecting said lipase extract.

2. A process for preparing a desalted lipase extract, comprising
    contacting adult rabbit stomach fundus with an acidic aqueous medium having a pH of 1.5 to 5, at a rate of 1 to 10 parts by volume of said acidic aqueous medium per part by weight of said fundus, at a temperature ranging from 4° to 30° C. and for a period of time ranging from 1 minute to 15 hours so as to obtain a solid material and an aqueous solution containing a lipase portion,
    separating said aqueous solution from said solid material so as to obtain a separate aqueous solution,
    adding to said separate aqueous solution 80-700 g/liter of ammonium sulfate and permitting said sulfate to remain in admixture with said separate aqueous medium for a time sufficient to salt out a lipase extract and to obtain a supernatant solution,
    separating the lipase extract from the supernatant solution,
    dissolving said lipase extract in an aqueous phase,
    filtering said aqueous phase on a membrane having a cutoff threshold between 5,000 and 10,000 daltons so as to obtain a solution of a desalted lipase extract and
    lyophilizing said desalted lipase extract solution to obtain said desalted lipase extract.

3. A process for preparing a purified lipase extract comprising
    contacting adult rabbit stomach fundus with an acidic aqueous medium having a pH ranging from 1.5 to 5, at a rate of 1 to 10 parts by volume of said acidic medium per part by weight of said fundus, at a temperature of 4° to 30° C. and for a period of time ranging from 1 minute to 15 hours so as to obtain a solid material and an aqueous solution containing a lipase portion, separating said aqueous solution from said solid material so as to obtain a separate aqueous solution, adding to said separate aqueous solution 80–700 g/liter of ammonium sulfate and permitting said sulfate to remain in admixture with said separate aqueous solution for a time sufficient to salt out a lipase extract and to obtain a supernatant solution, separating said lipase extract from said supernatant solution, dissolving said lipase extract in an aqueous phase, filtering said aqueous phase on a membrane having a cutoff threshold between 5,000 and 10,000 daltons so as to obtain a solution of a desalted lipase extract, lyophilizing said desalted lipase extract solution so as to obtain a desalted lipase extract and effecting a purification operation on said stomach fundus, said lipase extract or said desalted lipase extract.

4. A process for preparing a non-delipidated, enriched lipase extract comprising contacting adult rabbit stomach fundus with an acidic aqueous medium having a pH ranging from 1.5 to 5, at a rate of 1 to 10 parts by volume of said acidic aqueous medium per part by weight of said fundus, at a temperature of 4° to 30° C. and for a period of time ranging from 1 minute to 15 hours so as to obtain a solid material and an aqueous solution containing a lipase portion, separating said aqueous solution from said solid material so as to obtain a separate aqueous solution, adding to said separate aqueous solution 80–700 g/liter of ammonium sulfate and permitting said sulfate to remain in admixture with said separate aqueous solution for a time sufficient to salt out a lipase extract and to obtain a supernatant solution, separating said lipase extract from said supernatant solution, dissolving said lipase extract in a buffer having a pH ranging from 2 to 7 so as to obtain a buffered solution of said lipase extract, subjecting said buffered solution of said lipase extract having a pH ranging from 2 to 7 to chromatography on a molecular sieve whose exclusion limit exceeds 1,000,000 daltons, collecting an excluded elution fraction containing a non-delipidated, enriched lipase extract in buffered solution, filtering said excluded elution fraction on a membrane having a cutoff threshold of 10,000 daltons so as to obtain a desalted fraction and lyophilizing said desalted fraction so as to obtain said non-delipidated, enriched lipase extract.

5. A process for preparing a purified enriched lipase extract, comprising contacting adult rabbit stomach fundus with an acidic aqueous medium having a pH ranging from 1.5 to 5, at a rate of 1 to 10 parts by volume of said acidic medium per part by weight of said fundus, at a temperature of 4° to 30° C. and for a period of time ranging from 1 minute to 15 hours so as to obtain a solid material and an aqueous solution containing a lipase portion, separating said aqueous solution from said solid material so as to obtain a separate aqueous solution, adding to said separate aqueous solution 80–700 g/liter of ammonium sulfate and permitting said sulfate to remain in admixture with said separate aqueous solution for a time sufficient to salt out a lipase extract and to obtain a supernatant solution, separating said lipase extract from said supernatant solution, dissolving said lipase extract in water to obtain an aqueous solution containing said lipase extract, filtering said aqueous solution containing said lipase extract on a membrane having a cutoff threshold between 5,000 and 10,000 daltons to obtain a salt-free solution, adsorbing said salt-free solution on an ion exchange support, desorbing said support by an eluent, whose ionic strength is progressively increased as a function of time, collecting an elution fraction having a lipase activity and containing a purified, enriched lipase extract, filtering said elution fraction having a lipase activity on a membrane having a cutoff threshold between 5,000 and 10,000 daltons to obtain a desalted elution fraction and lyophilizing said desalted elution fraction so as to obtain said purified, enriched lipase extract.

6. A process for preparing a purified enriched lipase extract comprising homogenizing adult rabbit stomach fundus with acetone and further extracting with acetone, chloroform and diethyl ether to dilipidate said stomach fundus, dissolving powder derived from said delipidation step in an aqueous medium having a pH ranging from 1.5 to 5, at a temperature of 4° to 30° C. and for a period of time ranging from 1 minute to 15 hours so as to obtain a solid material and an aqueous solution containing a lipase portion, separating said aqueous solution from said solid material so as to obtain a separate aqueous solution, adding to said separate aqueous solution 80–700 g/liter of ammonium sulfate and permitting said sulfate to remain in admixture with said separate aqueous solution for a time sufficient to salt out a lipase extract and to obtain a supernatant solution, separating said lipase extract from said supernatant solution, dissolving said lipase extract in a buffer having a pH between 2 and 7 to obtain a buffered solution, subjecting said buffered solution to a molecular sieve having an upper exclusion limit of $2.5 \times 10^5$ daltons, collecting a retained elution fraction corresponding to a molecular weight between 30,000 and 55,000 daltons and containing a purified, enriched lipase extract, filtering said retained elution fraction corresponding to a molecular weight between 30,000 and 55,000 and containing said enriched lipase extract on a membrane having a cutoff threshold between 5,000 and 10,000 daltons so as to obtain a desalted, purified, enriched lipase extract solution and lyophilizing said desalted, purified, enriched lipase extract solution so as to obtain said purified enriched lipase extract.

7. A process for preparing a lipase, comprising homogenizing adult rabbit stomach fundus with acetone and further extracting with acetone, chloroform and diethyl ether to dilipidate said stomach fundus, dissolving powder derived from said delipidation step in an aqueous medium having a pH ranging from 1.5 to 5, at a temperature of 4° to 30° C. and for a period of time ranging form 1 minute to 15 hours so as to obtain a solid material and an aqueous solution containing a lipase portion, separating said aqueous solution from said solid material so as to obtain a separate aqueous solution, adding to said separate aqueous solution 80–700 g/liter of ammonium sulfate and permitting said sulfate to remain in admixture with said separate aqueous solution for a time sufficient to salt out a lipase extract and to obtain a supernatant solution, separating said lipase extract from said supernatant solution, dissolving said lipase extract in water so as to obtain an aqueous solution containing said lipase extract, filtering said aqueous solution containing said lipase extract on a membrane having a cutoff threshold between 5,000 and 10,000 daltons to obtain a salt-free solution, adsorbing said salt-free solution on an ion exchange support, desorbing said support by an eluent, whose ionic strength is progressively increased as a function of time, collecting an elution fraction having a lipase activity and containing a purified, enriched lipase extract, filtering said elution fraction having a lipase activity on a membrane having a cutoff threshold between 5,000 and 10,000 daltons to obtain a desalted elution fraction, subjecting said elution fraction to a molecular sieve having an upper exclusion limit of $2.5 \times 10^5$ daltons, collecting a retained elution fraction corresponding to a molecular weight between 45,000 and 50,000 daltons and containing said lipase, filtering said elution fraction containing said lipase on a membrane having a cutoff threshold of 5,000 to 10,000 daltons to obtain a desalted solution containing said lipase and, lyophilizing said desalted solution containing said lipase to obtain said lipase.

8. A process for preparing a lipase comprising homogenizing adult rabbit stomach fundus with acetone and further extracting with acetone, chloroform and diethyl ether to dilipidate said stomach fundus, dissolving powder derived from said delipidation step in an aqueous medium having a pH ranging from 1.5 to 5, at a temperature of 4° to 30° C. and for a period of time ranging form 1 minute to 15 hours so as to obtain a solid material and an aqueous solution containing a lipase portion, separating said aqueous solution from said solid material so as to obtain a separate aqueous solution, adding to said separate aqueous solution 80–700 g/liter of ammonium sulfate and permitting said sulfate to remain in admixture with said separate aqueous solution for a time sufficient to salt out a lipase extract and to obtain a supernatant solution, separating said lipase extract from said supernatant solution, dissolving said lipase extract in a buffer having a pH ranging from 2 to 7 to obtain a buffered solution, subjecting said elution fraction to a molecular sieve having an upper exclusion limit of $2.5 \times 10^5$ daltons, collecting a retained elution fraction corresponding to a molecular weight between 30,000 and 55,000 daltons and containing a purified, enriched lipase extract, adsorbing said retained elution fraction corresponding to a molecular weight between 30,000 and 55,000 daltons and containing said purified enriched lipase extract on an ion exchange support, desorbing said support by an eluent, whose ionic strength is progressively increased as a function of time, collecting an elution fraction having a lipase activity and containing said lipase, filtering said elution fraction having a lipase activity and containing said lipase on a membrane having a cutoff threshold of 5,000 to 10,000 daltons to obtain a desalted elution fraction containing said lipase and lyophilizing said desalted elution fraction containing said lipase to obtain said lipase.

9. The process of claim 1 comprising contacting said adult rabbit stomach fundus with an acidic aqueous medium at a temperature between 0° and 20° C.

10. The process of claim 1 comprising separating said aqueous solution from said solid material by filtration, decantation or centrifugation below 25° C.

11. The process of claim 1 wherein said ammonium sulfate is permitted to remain in admixture with said separate aqueous solution for a period of time ranging from 15 minutes to 20 hours at a temperature between 0° and 20° C.

12. The process of claim 1 which includes, prior to contacting said fundus with said acidic aqueous medium, fragmenting said fundus to a size below 1 cm.

13. A lipase having a molecular weight, according to the Laemmli method, of 49,000 daltons, whereof 9,000 correspond to sugars and 40,000 to a protein, the number of amino acid types being as follows:

Asp+Asn: 45; Thr: 19; Ser: 28; Glx: 30; Pro: 29; Gly: 25; Ala: 28; Val: 27; Met: 8; Ile: 18; Leu: 26; Tyr: 16; Phe: 18; Lys: 17; His: 7; Arg: 10; Cys: 9 and Trp: 6, containing the N-terminal sequence, Lys-Ser-Ala-Pro-Thr-Asn-Pro-Glu-Val-Asn-Met-X-Ile-Ser-Glu-Met-Ile-Ser-Tyr-Trp-Gly-Tyr-Ser-Glü-Pro-Lys-Tyr-Glu-Val-Val, wherein X represents an indeterminate amino acid, whose specific lipase activity, according to the Gargouri method, exceeds 1,000 U/mg of protein, whose maximum activity on tributyrin as substrate is obtained at a pH value of approximately 4.5, whose activity, at pH values of 3 and 7 is at least equal to half the maximum activity, which is still active after incubation for 2 hours at 37° C. and a pH value of 2, whose enzymatic activity is inhibited by cysteine reagents, which is able to resist pepsin, is degraded by chymotrypsin and by trypsin, whose isoelectric pH is between 5.7 and 7.1 and which is prepared from rabbit stomach fundus by a process comprising homogenizing adult rabbit stomach fundus with acetone and further extracting with acetone, chloroform and diethyl ether to dilipidate said stomach fundus, dissolving powder derived from said delipidation step in an aqueous medium having a pH ranging from 1.5 to 5, at a temperature of 4° to 30° C. and for a period of time ranging form 1 minute to 15 hours so as to obtain a solid material and an aqueous solution containing a lipase portion, separating said aqueous solution from said solid material so as to obtain a separate aqueous solution, adding to said separate aqueous solution 80–700 g/liter of ammonium sulfate and permitting said sulfate to remain in admixture with said separate aqueous solution for a time sufficient to salt out a lipase extract and to obtain a supernatant solution, separating said lipase extract from said supernatant solution, dissolving said lipase extract in water to obtain an aqueous solution containing said lipase extract, filtering said aqueous solution containing said lipase extract on a membrane having a cutoff threshold between 5,000 and 10,000 daltons to obtain a salt-free solution, adsorbing said salt-free solution on an ion exchange support, desorbing said support by an eluent, whose ionic strength is progressively increased as a function of time, collecting an elution fraction having a lipase activity and containing a purified, enriched lipase extract, filtering said elution fraction having a lipase activity on a membrane having a cutoff threshold between 5,000 and 10,000 daltons to obtain a desalted elution fraction, subjecting said elution fraction to a molecular sieve having an upper exclusion limit of $2.5 \times 10^5$ daltons, collecting a retained elution fraction corresponding to molecular weights between 45,000 and 50,000 daltons and containing said lipase, filtering said elution fraction containing said lipase on a membrane having a cutoff threshold of 5,000 to 10,000 daltons to obtain a desalted solution containing said lipase and lyophilizing said desalted solution containing said lipase to obtain said lipase.

14. A lipase having a molecular weight, according to the Laemmli method, of 49,000 daltons, whereof 9,000 correspond to sugars and 40,000 to a protein, the number of amino acid types being as follows:

Asp+Asn: 45; Thr: 19; Ser: 28; Glx: 30; Pro: 29; Gly: 25; Ala: 28; Val: 27; Met: 8; Ile: 18; Leu: 26; Tyr: 16; Phe: 18; Lys: 17; His: 7; Arg: 10; Cys: 9 and Trp: 6, containing the N-terminal sequence, Lys-Ser-Ala-Pro-Thr-Asn-Pro-Glu-Val-Asn-Met-X-Ile-Ser-Glu-Met-Ile-Ser-Tyr-Trp-Gly-Tyr-Ser-Glü-Pro-Lys-Tyr-Glu-Val-Val, wherein X represents an indeterminate amino acid, whose specific lipase activity, according to the Gargouri method, exceeds 1,000 U/mg of protein, whose maximum activity on tributyrin as substrate is obtained at a pH value of approximately 4.5, whose activity, at pH values of 3 and 7 is at least equal to half the maximum activity, which is still active after incubation for 2 hours at 37° C. and a pH value of 2, whose enzymatic activity is inhibited by cysteine reagents, which is able to resist pepsin, is degraded by chymotrypsin and by trypsin, whose isoelectric pH is between 5.7 and 7.1 and which is prepared from adult rabbit stomach fundus by a process comprising homogenizing adult rabbit stomach fundus with acetone and further extracting with acetone, chloroform and diethyl ether to dilipidate said stomach fundus, dissolving powder derived from said delipidation step in an aqueous medium having a pH ranging from 1.5 to 5, at a temperature of 4° to 30° C. and for a period of time ranging form 1 minute to 15 hours so as to obtain a solid material and an aqueous solution containing a lipase portion, separating said aqueous solution from said solid material so as to obtain a separate aqueous solution, adding to said separate aqueous solution 80–700 g/liter of ammonium sulfate and permitting said sulfate to remain in admixture with said separate aqueous solution for a time sufficient to salt out a lipase extract and to obtain a supernatant solution, separating said lipase extract from said supernatant solution, dissolving said lipase extract in a buffer having a pH between 2 and 7 to obtain a buffered solution, subjecting said elution fraction to a molecular sieve having an upper exclusion limit of $2.5 \times 10^5$ daltons, collecting a retained elution fraction corresponding to molecular weights between 30,000 and 55,000 daltons and containing a purified, enriched lipase extract, adsorbing said retained elution fraction corresponding to molecular weights between 30,000 and 55,000 daltons and containing said purified enriched lipase extract on an ion exchange support, desorbing said support by an eluent, whose ionic strength is progressively increased as a function of time, collecting an elution fraction having a lipase activity and containing said lipase, filtering said elution fraction having a lipase activity and containing said lipase on a membrane having a cutoff threshold of 5,000 to 10,000 daltons to obtain a desalted elution fraction containing said lipase and lyophilizing said desalted elution fraction containing said lipase to obtain said lipase.

15. A lipase having a specific lipase activity, according to the Gargouri method, exceeding 1,000 U/mg of protein, whose maximum activity on tributyrin as substrate is obtained at a pH value of approximately 4.5, whose activity, at pH values of 3 and 7, is at least equal to half the maximum activity, which is still active after incubation for 2 hours at 37° C. at a pH value of 2 and which is prepared from adult rabbit stomach fundus by a process comprising homogenizing adult rabbit stomach fundus with acetone and further extracting with acetone, chloroform and diethyl ether to dilipidate said stomach fundus, dissolving powder derived from said delipidation step in an aqueous medium having a pH ranging from 1.5 to 5, at a temperature of 4° to 30° C. and for a period of time ranging form 1 minute to 15 hours so as to obtain a solid material and an aqueous solution containing a lipase portion, separating said aqueous solution from said solid material so as to obtain a separate aqueous solution, adding to said separate aqueous solution 80–700 g/liter of ammonium sulfate and permitting said sulfate to remain in admixture with said separate aqueous solution for a time sufficient to salt out a lipase extract and to obtain a supernatant solution, separating said lipase extract from said supernatant solution, dissolving said lipase extract in a buffer having a pH between 2 and 7 to obtain a buffered solution, subjecting said elution fraction to a molecular sieve having an upper exclusion limit of $2.5 \times 10^5$ daltons, collecting a retained elution fraction corresponding to molecular weights between 30,000 and 55,000 daltons and containing a purified, enriched lipase extract, adsorbing said retained elution fraction corresponding to molecular weights between 30,000 and 55,000 daltons and containing said purified enriched lipase extract on an ion exchange support, desorbing said support by an eluent, whose ionic strength is progressively increased as a function of time, collecting an elution fraction having a lipase activity and containing said lipase, filtering said elution fraction having a lipase activity and containing said lipase on a membrane having a cutoff threshold of 5,000 to 10,000 daltons to obtain a desalted elution fraction containing said lipase and lyophilizing said desalted elution fraction containing said lipase to obtain said lipase.

16. Non-delipidated enriched lipase extract having a specific lipase activity, according to the Gargouri method, between 100 and 1,000 U/mg of protein, whose maximum activity on tributyrin as substrate is obtained at a pH value of approximately 4.5, whose activity, at pH values of 3 and 7, is at least equal to half the maximum activity, which is still active after an incubation for 2 hours at 37° C. and a pH value of 2, which resists pepsin, which is degraded by chymotrypsin and by trypsin, whose enzymatic activity is inhibited by cysteine reagents and which is prepared from adult rabbit stomach fundus by a process comprising homogenizing adult rabbit stomach fundus with acetone and further extracting with acetone, chloroform and diethyl ether to dilipidate said stomach fundus, dissolving powder derived from said delipidation step in an aqueous medium having a pH ranging from 1.5 to 5, at a temperature of 4° to 30° C. and for a period of time ranging form 1 minute to 15 hours so as to obtain a solid material and an aqueous solution containing a lipase portion, separating said aqueous solution from said solid material so as to obtain a separate aqueous solution, adding to said separate aqueous solution 80–700 g/liter of ammonium sulfate and permitting said sulfate to remain in admixture with said separate aqueous solution for a time sufficient to salt out a lipase extract and to obtain a supernatant solution, separating said lipase extract from said supernatant solution, dissolving said lipase extract in a buffer having a pH between 2 and 7 to obtain a buffered solution, subjecting said elution fraction to a molecular sieve having an upper exclusion limit of $2.5 \times 10^5$ daltons, collecting an excluded elution fraction containing non-delipidated, enriched lipase extract in buffered solution, filtering said excluded elution fraction on a membrane having a cutoff threshold of 10,000 daltons to obtain a desalted fraction and lyophilizing said desalted fraction to obtain said non-delipidated, enriched lipase extract.

17. Lipase extract having a specific lipase activity, according to the Gargouri method, between 1 and 100 U/mg of protein, whose maximum activity on tributyrin as substrate is obtained for a pH value of approximately 4.5, whose activity, at pH values of 3 and 7, is at least equal to half the maximum activity, which is still active after incubation for 2 hours at 37° C. and a pH value of 2, which resists pepsin, which is degraded by chymotrypsin and by trypsin, whose enzymatic activity is inhibited by cysteine reagents and which is prepared by a process comprising contacting adult rabbit stomach fundus with an acidic aqueous medium having a pH ranging from 1.5 to 5, at a rate of 1 to 10 parts by volume of said acidic aqueous medium per part by weight of said fundus, at a temperature of 4° to 30° C. and for a period of time ranging from 1 minute to 15 hours to obtain a solid material and an aqueous solution containing a lipase portion, separating said aqueous solution from said solid material to obtain a separate aqueous solution, adding to said separate aqueous solution 80–700 g/liter of ammonium sulfate and permitting said sulfate to remain in admixture with said separate aqueous solution for a time sufficient to salt out said lipase extract and to obtain a supernatant solution, separating said lipase extract from said supernatant solution and collecting said lipase extract.

18. Medicament for controlling the malabsorption of fatty substances in men and animals, comprising as the active principle a lipase having a molecular weight, according to the Laemmli method, of 49,000 daltons, whereof 9,000 correspond to sugars and 40,000 to a protein, the number of amino acid types being as follows:

Asp+Asn: 45; Thr: 19; Ser: 28; Glx: 30; Pro: 29; Gly: 25; Ala: 28; Val: 27; Met: 8; Ile: 18; Leu: 26; Tyr: 16; Phe: 18; Lys: 17; His: 7; Arg: 10; Cys: 9 and Trp: 6, whereof the N-terminal sequence is: Lys-Ser-Ala-Pro-Thr-Asn-Pro-Glu-Val-Asn-Met-X-Ile-Ser-Glu-Met-Ile-Ser-Tyr-Trp-Gly-Tyr-Ser-Glu-Pro-Lys-Tyr-Glu-Val-Val, wherein X represents an indeterminate amino acid, whose specific lipase activity, according to the Gargouri method, exceeds 1,000 U/mg of protein, whose maximum activity on tributyrin as substrate is obtained at a pH value of approximately 4.5, whose activity, at pH values of 3 and 7, is at least equal to half the maximum activity, which is still active after incubation for 2 hours, at 37° C. and a pH value of 2, whose enzymatic activity is inhibited by cysteine reagents, which is able to resist pepsin, is degraded by chymotrypsin and by trypsin, whose isoelectric pH is between 5.7 and 7.1 and which is prepared from adult rabbit stomach fundus by a process comprising homogenizing adult rabbit stomach fundus with acetone and further extracting with acetone, chloroform and diethyl ether to dilipidate said stomach fundus, dissolving powder derived from said delipidation step in an aqueous medium having a pH ranging from 1.5 to 5, at a temperature of 4° to 30° C. and for a period of time ranging form 1 minute to 15 hours so as to obtain a solid material and an aqueous solution containing a lipase portion, separating said aqueous solution from said solid material to obtain a separate aqueous solution, adding to said separate aqueous solution 80-700 g/liter of ammonium sulfate and permitting said sulfate to remain in admixture with said separate aqueous solution for a time sufficient to salt out a lipase extract and to obtain a supernatant solution, separating said lipase extract from said supernatant solution, dissolving said lipase extract in water to obtain an aqueous solution containing said lipase extract, filtering said aqueous solution containing said lipase extract on a membrane having a cutoff threshold between 5,000 and 10,000 daltons to obtain a salt-free solution, adsorbing said salt-free solution on an ion exchange support, desorbing said support by an eluent, whose ionic strength is progressively increased as a function of time, collecting an elution fraction having a lipase activity and containing a purified, enriched lipase extract, filtering said elution fraction having a lipase activity on a membrane having a cutoff threshold between 5,000 and 10,000 daltons to obtain a desalted elution fraction, subjecting said elution fraction to a molecular sieve having an upper exclusion limit of $2.5 \times 10^5$ daltons, collecting a retained elution fraction corresponding to molecular weights between 45,000 and 50,000 daltons and containing said lipase, filtering said elution fraction containing said lipase on a membrane having a cutoff threshold of 5,000 to 10,000 daltons to obtain a desalted solution containing said lipase and lyophilizing said desalted solution containing said lipase to obtain said lipase.

19. Medicament for controlling the malabsorption of fatty substances in men and animals, comprising as the active principle a lipase having a molecular weight, according to the Laemmli method, of 49,000 daltons, whereof 9,000 correspond to sugars and 40,000 to a protein, the number of amino acid types being as follows:

Asp+Asn: 45; Thr: 19; Ser: 28; Glx: 30; Pro: 29; Gly: 25; Ala: 28; Val: 27; Met: 8; Ile: 18; Leu: 26; Tyr: 16; Phe: 18; Lys: 17; His: 7; Arg: 10; Cys: 9 and Trp: 6, containing the N-terminal sequence, Lys-Ser-Ala-Pro-Thr-Asn-Pro-Glu-Val-Asn-Met-X-Ile-Ser-Glu-Met-Ile-Ser-Tyr-Trp-Gly-Tyr-Ser-Glü-Pro-Lys-Tyr-Glu-Val-Val, wherein X represents an indeterminate amino acid, whose specific lipase activity, according to the Gargouri method, exceeds 1,000 U/mg of protein, whose maximum activity on tributyrin as substrate is obtained at a pH value of approximately 4.5, whose activity, at pH values of 3 and 7 is at least equal to half the maximum activity, which is still active after incubation for 2 hours at 37° C. and a pH value of 2, whose enzymatic activity is inhibited by cysteine reagents, which is able to resist pepsin, is degraded by chymotrypsin and by trypsin, whose isoelectric pH is between 5.7 and 7.1 and which is prepared from adult rabbit stomach fundus by a process comprising homogenizing adult rabbit stomach fundus with acetone and further extracting with acetone, chloroform and diethyl ether to dilipidate said stomach fundus, dissolving powder derived from said delipidation step in an aqueous medium having a pH ranging from 1.5 to 5, at a temperature of 4° to 30° C. and for a period of time ranging form 1 minute to 15 hours so as to obtain a solid material and an aqueous solution containing a lipase portion, separating said aqueous solution from said solid material so as to obtain a separate aqueous solution, adding to said separate aqueous solution 80-700 g/liter of ammonium sulfate and permitting said sulfate to remain in admixture with said separate aqueous solution for a time sufficient to salt out a lipase extract and to obtain a supernatant solution, separating said lipase extract from said supernatant solution, dissolving said lipase extract in a buffer having a pH between 2 and 7 to obtain a buffered solution, subjecting said elution fraction to a molecular sieve having an upper exclusion limit of $2.5 \times 10^5$ daltons, collecting a retained elution fraction corresponding to molecular weights between 30,000 and 55,000 daltons and containing a purified, enriched lipase extract, adsorbing said retained elution fraction corresponding to molecular weights between 30,000 and 55,000 daltons and containing said purified enriched lipase extract on an ion exchange support, desorbing said support by an eluent, whose ionic strength is progressively increased as a function of time, collecting an elution fraction having a lipase activity and containing said lipase, filtering said elution fraction having a lipase activity and containing said lipase on a membrane having a cutoff threshold of 5,000 to 10,000 daltons to obtain a desalted elution fraction containing the said lipase and lyophilizing said desalted elution fraction containing said lipase to obtain said lipase.

20. Medicament for controlling the malabsorption of fatty substances in men and animals, comprising as the active principle a lipase whose specific lipase activity, according to the Gargouri method, exceeds 1,000 U/mg of protein, whose maximum activity on tributyrin as substrate is obtained at a pH value of approximately 4.5, whose activity at pH values of 3 and 7, is at least equal to half the maximum activity, which is still active after incubation for 2 hours at 37° C. and at a pH value of 2 and which is prepared from adult rabbit stomach fundus by a process comprising homogenizing adult rabbit stomach fundus with acetone and further extracting with acetone, chloroform and diethyl ether to dilipidate said stomach fundus, dissolving powder derived from said delipidation step in an aqueous medium having a pH ranging from 1.5 to 5, at a temperature of 4° to 30° C. and for a period of time ranging form 1 minute to 15 hours so as to obtain a solid material and an aqueous solution containing a lipase portion, separating said aqueous solution from said solid material so as to obtain a separate aqueous solution, adding to said separate aqueous solution 80-700 g/liter of ammonium sulfate and permitting said sulfate to remain in admixture with said separate aqueous solution for a time sufficient to salt out a lipase extract and to obtain a supernatant solution, separating said lipase extract from said supernatant solution, dissolving said lipase extract in a buffer having a pH between 2 and 7 to obtain a buffered solution, subjected said elution fraction to a molecular sieve having an upper exclusion limit of $2.5 \times 10^5$ daltons, collecting a retained elution fraction corresponding to molecular weights between 30,000 and 55,000 daltons and containing a purified, enriched lipase extract, adsorbing said retained elution fraction corresponding to molecular weights between 30,000 and 55,000 daltons and containing said purified enriched lipase extract on an ion exchange support, desorbing said support by an eluent, whose ionic strength is progressively increased as a function of time, collecting an elution fraction having a lipase activity and containing said lipase, filtering said elution fraction having a lipase activity and containing said lipase on a membrane having a cutoff threshold of 5,000 to 10,000 daltons to obtain a desalted elution fraction containing said lipase and lyophilizing said desalted elution fraction containing said lipase to obtain said lipase.

21. Medicament for controlling the malabsorption of fatty substances in men and animals, comprising as the active principle an enriched lipase extract having a specific lipase activity, according to the Gargouri method, between 100 and 1,000 U/mg of protein, whose maximum activity on tributyrin as substrate is obtained at a pH value of approximately 4.5, whose activity, at pH values of 3 and 7, is at least equal to half the maximum activity, which is still active after incubation for 2 hours at 37° C. and a pH value of 2, which resists pepsin, which is degraded by chymotrypsin and by trypsin, whose enzymatic activity is inhibited by cysteine reagents and which is prepared by a process comprising contacting adult rabbit stomach fundus with an acidic aqueous medium having a pH ranging from 1.5 to 5, at a rate of 1 to 10 parts by volume of said acidic aqueous medium per part by weight of said fundus, at a temperature of 4° to 30° C. and for a period of time ranging from 1 minute to 15 hours so as to obtain a solid material and an aqueous solution containing a lipase portion, separating said aqueous solution from said solid material so as to obtain a separate aqueous solution, adding to said separate aqueous solution 80–700 g/liter of ammonium sulfate and permitting said sulfate to remain in admixture with said separate aqueous solution for a time sufficient to salt out a lipase extract and to obtain a supernatant solution, separating said lipase extract from said supernatant solution, dissolving said lipase extract in a buffer having a pH between 2 and 7 to obtain a buffered solution, subjecting said buffered solution having a pH between 2 and 7 to chromatography on a molecular sieve, whose exclusion limit exceeds 1,000,000 daltons, collecting an excluded elution fraction containing non-delipidated, enriched lipase extract in buffered solution, filtering said excluded elution fraction on a membrane having a cutoff threshold of 10,000 daltons to obtain a desalted fraction and lyophilizing said desalted fraction to obtain said non-delipidated, enriched lipase extract.

22. Medicament for controlling the malabsorption of fatty substances in men and animals, comprising as the active principle a lipase extract having a specific lipase activity, according to the Gargouri method, between 1 and 100 U/mg of protein, whose maximum activity on tributyrin as substrate is obtained for a pH value of approximately 4.5, whose activity, at pH values of 3 and 7, is at least equal to half the maximum activity, which is still active after incubation for 2 hours at 37° C. and a pH value of 2, which resists pepsin, which is degraded by chymotrypsin and by trypsin, whose enzymatic activity is inhibited by cysteine reagents and which is prepared by a process comprising contacting adult rabbit stomach fundus with an acidic aqueous medium having a pH ranging from 1.5 to 5, at a rate of 1 to 10 parts by volume of said acidic aqueous medium per part by weight of said fundus, at a temperature of 4° to 30° C. and for a period of time ranging from 1 minute to 15 hours so as to obtain a solid material and an aqueous solution containing a lipase portion, separating said aqueous solution from said solid material so as to obtain a separate aqueous solution, adding to said separate aqueous solution 80–700 g/liter of ammonium sulfate and permitting said sulfate to remain in admixture with said separate aqueous solution for a time sufficient to salt out a lipase extract and to obtain a supernatant solution, separating said lipase extract from said supernatant solution and collecting said lipase extract.

* * * * *